(12) United States Patent
Takeo

(10) Patent No.: US 6,718,547 B2
(45) Date of Patent: *Apr. 6, 2004

(54) MEDICAL NETWORK SYSTEM

(75) Inventor: Hideya Takeo, Kanagawa-ken (JP)

(73) Assignee: Fuji Photo Film Co., Ltd., Kanagawa-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/245,337

(22) Filed: Feb. 5, 1999

(65) Prior Publication Data

US 2002/0092006 A1 Jul. 11, 2002

(30) Foreign Application Priority Data

Feb. 17, 1998 (JP) .......................................... 10/034412

(51) Int. Cl.⁷ ................................................ G06F 9/44
(52) U.S. Cl. ...................................... 717/170; 717/173
(58) Field of Search .................... 717/11, 1, 168–178; 707/203; 709/200, 203, 232

(56) References Cited

U.S. PATENT DOCUMENTS

| | | | | |
|---|---|---|---|---|
| 4,558,413 A | * | 12/1985 | Schmidt et al. .............. 707/203 |
| 5,452,407 A | * | 9/1995 | Crook ......................... 345/421 |
| 5,528,490 A | * | 6/1996 | Hill ............................. 717/168 |
| 6,006,034 A | * | 12/1999 | Heath et al. ................... 717/11 |
| 6,021,404 A | * | 2/2000 | Moukheibir .................. 706/46 |
| 6,141,683 A | * | 10/2000 | Kraml et al. ................. 709/220 |
| 6,167,567 A | * | 12/2000 | Chiles et al. ................. 717/11 |
| 6,199,204 B1 | * | 3/2001 | Donohue ...................... 717/11 |
| 6,205,579 B1 | * | 3/2001 | Southgate .................... 717/11 |

* cited by examiner

Primary Examiner—Wei Zhen
(74) Attorney, Agent, or Firm—Sughrue Mion, PLLC

(57) ABSTRACT

Software components installed in each medical device composing a medical network system is replaced efficiently and the service load on a software producer which provides the software component is reduced. A component server for storing and managing the latest versions of the software components is connected via the network to each medical device composing the medical network system. At a predetermined timing such as upon starting the medical devices for example, each medical device accesses the component server via the network or vice versa. Whether or not the component installed in each device is the latest version is checked, and the latest version is transferred from the component server to the medical device when the component is not the latest version. The medical device is then restarted.

1 Claim, 4 Drawing Sheets

MEDICAL NETWORK SYSTEM

BACKGROUND OF THE INVENTION

1. Field of the Invention

The present invention relates to a medical network system wherein various kinds of medical devices are connected to a network.

2. Description of the Related Art

Various kinds of image processing have been carried out on images recorded by various kinds of imaging modalities such as the ones for CT, MRI and CR so that the images become appropriate for diagnosis. Such image processing is usually carried out by medical application software incorporated in each medical device.

The version of such medical application software is sometimes updated in order to improve its function or for debugging. For general purpose equipment such as a workstation, such upgrading is carried out by installation of new software from a recording medium such as a floppy disc. For dedicated equipment in which software is recorded and incorporated in a ROM, the ROM is replaced. However, in the case of medical application on software, special knowledge and technique are needed to replace such software, and the replacement of the software might affect reliability and safetiness of the devices. Accordingly, the replacement work cannot be easily and freely carried out by users like general personal computer. Such a software replacing operation is usually carried out manually by a service person of the company producing the software.

Recently, medical network systems have been increasing. In a medical network system, imaging modalities such as a CT apparatus, a laser printer for outputting an image, a server computer for storing and managing the image (hereinafter called an image server), and a diagnosis terminal for diagnosing the image are connected to a network, and doctors and radiologists or staff for clinical examination can exchange an image for diagnosis as digital data to improve efficiency in hospital operations.

Furthermore, following the reduction in personal computer prices, each doctor is often assigned to a personal computer, and the number of items of equipment composing the network system is thus increasing.

As has been described in the above, manual replacement of software for a medical network system having a large number of components by a service person is a great burden on a software producer.

Therefore, realization of a medical network system wherein software replacement therefor is efficient has been desired.

SUMMARY OF THE INVENTION

The present invention reduces a load on a service for a medical network system by automating replacement of software components thereof.

In other words, the medical network system of the present invention connects on a network a plurality of medical devices each of which is loaded with at least one software component, and comprises:

component storing means which is connected to the network and stores and manages the latest version of each software component;

version comparing means for comparing, for each software component, the version of the software component installed in each medical device with that of the software component stored and managed by the component storing means;

component replacing means for replacing the software component installed in the medical device by transferring the latest version of the software component from the component storing means to the medical device when the version of the software component installed in the medical device is found to be older than that of the software component stored and managed by the component storing means as a result of comparison by the version comparing means; and restart means for restarting the medical device at least one software component of which has been replaced by the component replacing means.

The medical network system in accordance with the present invention may further have restart means for restarting medical devices in which at least one software components is replaced by said component replacing means.

The "software component" herein referred to means a program, a data file, or the like for realizing a variety of functions of the medical network system such as image processing and communication processing. One function is realized by one software component in some cases, or by a plurality of software components in other cases. Software replacement can be carried out for each software component.

The "medical devices" mean various kinds of devices composing the medical network system, such as imaging modalities, workstations for diagnosis, personal computers for image reference.

The "component storing means" means a database managing the latest versions of software or a computer loaded with such a database. The situation wherein the component storing means is "connected to the network" may mean the case where the component storing means is connected by a dial-up connection or the like (that is, the component storing means can be connected upon necessity).

The "version comparing means", the "component replacing means" and the "restart means" are groups of programs installed distributively in a computer managing the components as well as in each of the medical devices. The groups of programs have two types, that is, a type wherein each medical device is a client and the other type wherein the computer managing the components is a client. Further, in the case where the restart means is not provided, the part as to restart is omitted in the following description of the two forms.

In the form wherein each medical device is a client, each medical device accesses, on start-up, the computer storing the components and carries out the version comparison for each of the components. When the versions disagree, the latest version is downloaded and the medical device restarts. In this case, the computer managing the components has a function to notify the latest version to the medical device which has accessed to the computer and a server function which transfers the latest version of the component.

Meanwhile, in the form wherein the computer managing the components is a client, the computer obtains the version of each component at start-up by sequentially accessing each medical device, and compares the obtained version with the version stored therein. When the two do not agree, the latest version is transferred to the medical device and the medical device is requested to restart. In this case, each medical device has a function to notify the version of a component having been installed therein to the client and a function to restart upon request.

In each case, the timing of the version comparison is the time when each medical device or the computer managing the components starts up, or a pre-set time, or the time that an operator instructs, for example. The version comparison may be carried out regularly at a pre-set interval such as at every 24 hours.

"Start" or "restart" means the start of a medical application program for realizing the medical network system. In other words, the "start" time means not only the time when power is switched on but also the time an application program is started with power having been switched on. Likewise, "restart" means not only the case where power is switched on again but also the case where only an application program is restarted.

The medical network system of the present invention judges whether or not the software component installed in each medical device composing the system is the latest version at a predetermined timing, and replaces the software component automatically with the latest version if the software component is not the latest version. In this manner, unlike a conventional system, manual replacement of a software component for each medical device is not necessary, and the load on a software producer which provides the software component is greatly reduced.

DESCRIPTION OF THE PREFERRED EMBODIMENTS

Figure 1:
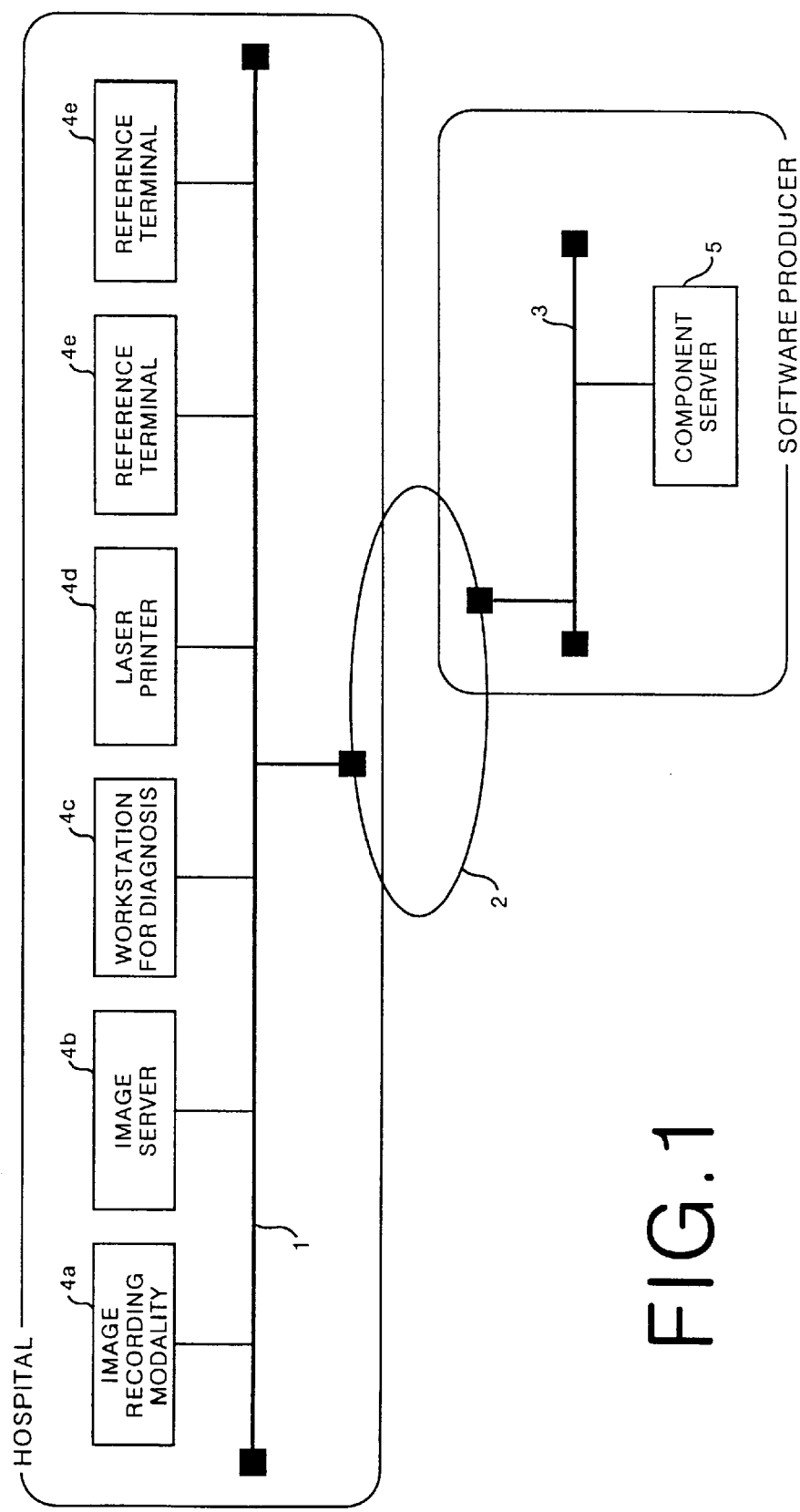
FIG. 1 is a diagram showing an embodiment of a medical network system of the present invention.

Hereinafter, a medical network system of the present invention will be explained with reference to the accompanying drawings. FIG. 1 shows an embodiment of the medical network system of the present invention.

In the system shown in FIG. 1, a network 1 is a Local Area Network (LAN) such as Ethernet or FDDI, installed in a hospital. In this case, the LAN is connected to the Internet 2 via a dedicated line or a public telecommunication line such as ISDN. An image recording modality 4a, an image server 4b, a workstation 4c for diagnosis, a laser printer 4d, and tens or hundreds of reference terminals 4e are connected to the network 1 as medical devices composing the medical network system. The image recording modality 4a is an apparatus or a system for recording an image related to a patient as digital data, such as a CT, MRI, RI, or US apparatus. The image recording modality may record analogue signals of an image obtained by photographing, after converting the signal into digital signals. Alternatively, the image recording modality may obtain digital data by reading an image photographed on a film or the like.

The image server 4b is a computer which stores, in an image database, image data recorded by the image recording modality 4a. In this case, the image server 4b carries out image processing such as sharpness enhancement on the image data before storing the data.

Among the image data stored in the image server 4b, the image server 4b searches for image data requested by the workstation 4c for diagnosis or by one of the reference terminals 4e, reads out the image data from the database, and provides the image data to the workstation 4c or to the reference terminal 4e.

The workstation 4c for diagnosis is a terminal used by a doctor in a radiological ward or the like, for referring to the image data, for carrying out image processing thereon by changing an image processing parameter upon necessity so that the image becomes appropriate for diagnosis, and for diagnosing with reference to the processed image.

The laser printer 4d outputs processed image data as a visible image. Output of image data to the laser printer 4d is carried out by an instruction given from the workstation 4c for diagnosis to the image server 4b. The reference terminals 4e are installed only for referring to image data.

Each of medical devices 4 such as the ones described in the above has one or a plurality of software components. For example, the image recording modality 4a is loaded with a control program and photographing condition data for controlling photographing processing or film reading processing. The workstation 4c for diagnosis has components such as an image processing program, parameters for image processing, and a printer driver for the laser printer 4d, for example. For example, in the CR wherein a radiographic image information is recorded on a stimulable phosphor sheet, the sheet is scanned by stimulating light and the light emitted by the sheet upon exposure to the scanning is read out by a photo electric detector to obtain an image signal, various function control programs such as the one to control the function of the read-out device such as transfer of stimulable phosphor sheet, stimulating light scanning and emitted light read-out, various image processing programs for automatic control of the density and contrast, gradation processing, frequency processing, dynamic range compression processing, and various parameters therefor correspond to said components. Replacement of a software component can be carried out for each software component.

Meanwhile, a component server 5 in FIG. 1 is a server computer for storing and managing the latest version of each component. The component server 5 is connected to a network 3 of a software producer which provides the software, as shown in FIG. 1. Furthermore, the component server 5 is also connected to the network 1 in the hospital via the Internet 2.

Figure 2:
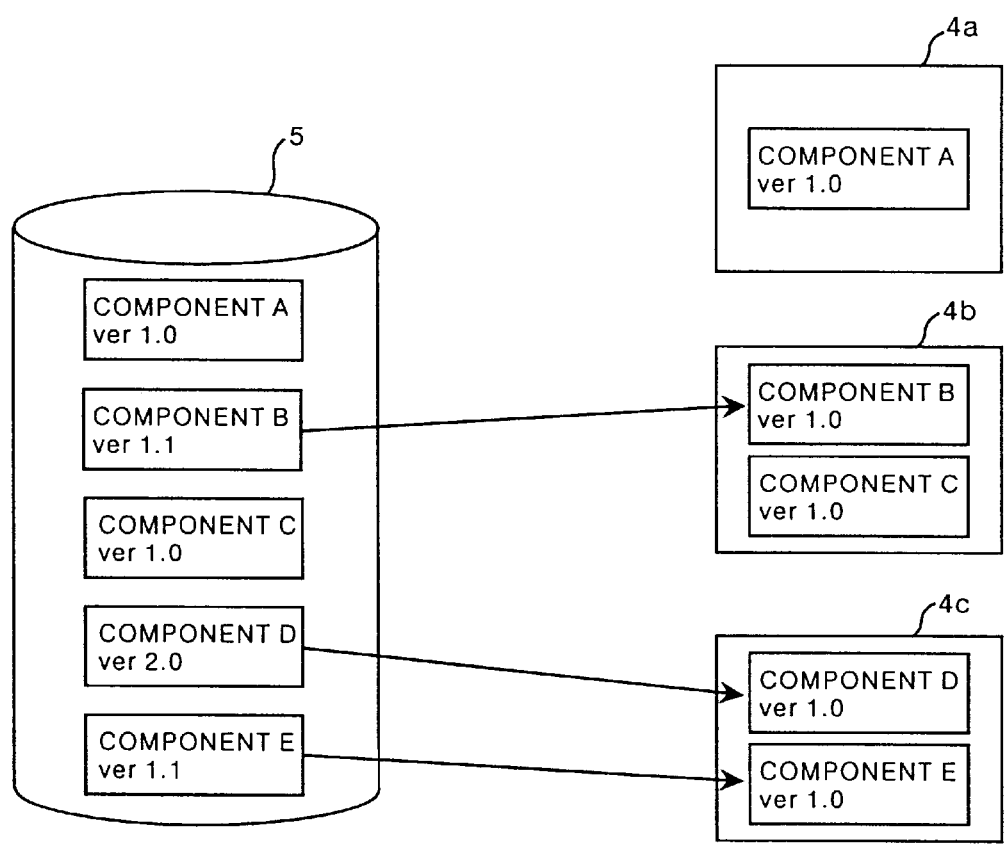
FIG. 2 is a diagram showing a role of a component server.

FIG. 2 shows a role of the component server 5. For example, assume that the medical devices 4a, 4b, and 4c connected to the network 1 in the hospital have a component A of version 1.0, a component B of version 1.0 as well as a component C of version 1.0, and a component D of version 1.0 as well as a component E of version 1.0, respectively.

The component server 5 stores and manages the components A through E. The software producer changes the components stored in the component server 5 to the latest versions thereof whenever the software producer carries out upgrade of the components. In the example shown in FIG. 2, the components B, D and E are updated.

Figure 3:
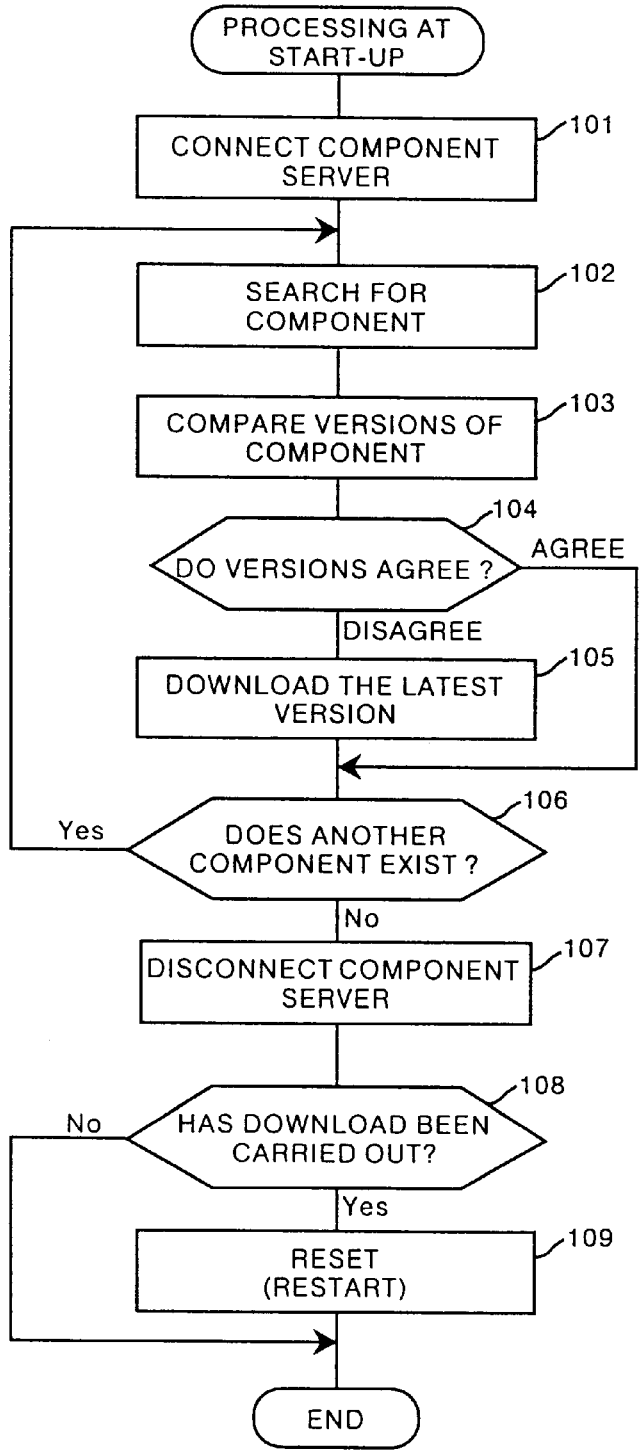
FIG. 3 is a flow chart showing an example of component replacing processing.

FIG. 3 is a flow chart showing an example of processing carried out upon the replacement of the components shown in FIG. 2. In the example shown in FIG. 3, processing at the start of each medical device is shown. However, in the case where the medical devices 4 are operating 24 hours a day for example, the same processing may be carried out by an instruction of an operator or regularly at a predetermined interval.

Each of the medical devices 4 connects itself to the component server 5 via the network 1, the Internet 2, and the network 3 upon its start (Step 101), and searches for a component installed in the medical device among the components stored by the component server 5 (Step 102). The version of the component found through the search is compared with that of the component actually installed in the medical device (Step 103). When the two do not agree (Step 104), the latest version having been searched for is downloaded (Step 105), and the processing from Step 102 through Step 105 is repeated for another component in the medical device (Step 106). When the versions agree at Step 104, no downloading is carried out and the processing from Step 102 through Step 105 is repeated for another component (Step 106).

After the version comparison and downloading of the latest version have been finished for all components installed in the medical devices, the medical devices 4 disconnect the component server 5 (step 107). Only when downloading of the latest version is carried out for any one of the components (Step 108), is the entire apparatus or the application program reset (Step 109). However, whether only the program or the entire apparatus is restarted depends on the kind of component.

Through the above processing, the latest version 1.1 of the component B is downloaded to the medical device 4b, and the latest versions 2.0 and 1.1 for the components D and E respectively are downloaded to the medical device 4c, as shown in FIG. 2. The medical devices 4b and 4c are then restarted. In this case, the medical device 4a is not restarted since no replacement of its component has been carried out.

FIG. 3 is a flow chart showing the processing for the case where the medical devices 4 are clients and access the component server 5. On the contrary, the component server 5 may access each of the medical devices 4. For example, when a parameter adjusted independently for each of the medical devices 4 is managed, the form wherein the component server 5 accesses the medical devices is more convenient.

As has been described in the above, according to the system of the present invention, replacement of the component is carried out automatically. Therefore, the software producer providing the software components only has to store the latest-version component in the component server managed by the software producer, and does not need to dispatch a service person to a customer.

Figure 4:
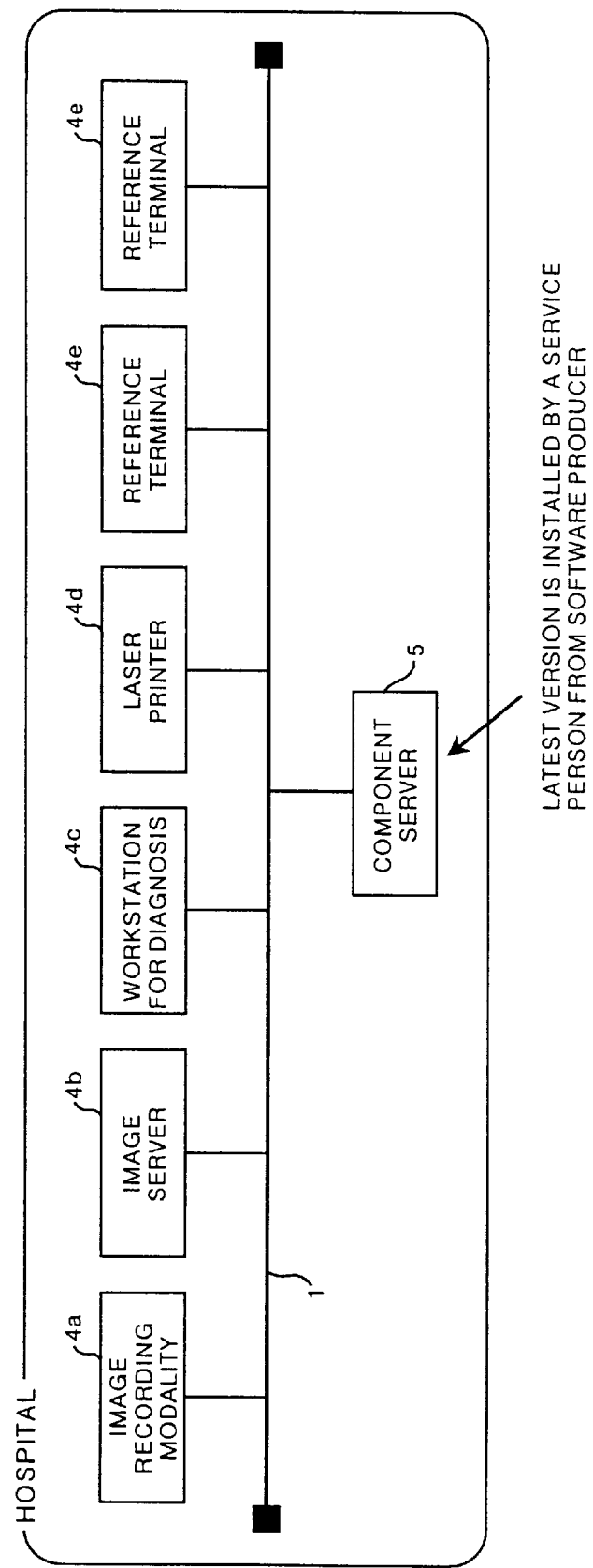
FIG. 4 is a diagram showing another embodiment of the medical network system of the present invention.

Depending on hospitals, no connection to the outside such as to the Internet may be available, in order to prevent leakage of information regarding patients or diagnoses. In such a case, as shown in FIG. 4, the component server 5 is connected to the network 1 in the hospital and a service person from the software producer installs the software components only in the component server 5. In this case, since a service person needs to be sent, the load on the software producer is heavier than in the case of the embodiment shown in FIG. 1. However, the load is reduced compared to a conventional system wherein the installation is carried out on each medical device.

What is claimed is:

1. A medical network system which connects on a network a plurality of medical devices each of which is loaded with at least one software component, the medical network system comprising:

component storing means which is connected to the network and stores and manages the latest version of each software component;

version comparing means for comparing, for each software component, the version of the software component installed in each medical device with that of the software component stored and managed by the component storing means;

component replacing means for replacing the software component installed in the medical device by transferring the latest version of the software component from the component storing means to the medial device when the version of the software component installed in the medical device is found to be older than that of the software component stored and managed by the component storing means as a result of the comparison by the version comparing means, wherein said plurality of medical devices, the component storing means, the version comparing means and the component replacing means are interconnected via a Local Area Network wherein said component storing means acts as a client in a client-server relationship; and wherein said component storing means sequentially accesses each of said medical devices in order to trigger said comparing.

\* \* \* \* \*